| United States Patent [19] | [11] | 4,150,035 |
|---|---|---|
| Asato | [45] | Apr. 17, 1979 |

[54] SUBSTITUTED TETRAHYDROBENZOTHIOPHENES AND METHOD OF PREPARATION THEREOF

[75] Inventor: Goro Asato, Titusville, N.J.

[73] Assignee: American Cyanamid Company, Stamford, Conn.

[21] Appl. No.: 912,809

[22] Filed: Jun. 5, 1978

Related U.S. Application Data

[63] Continuation of Ser. No. 684,701, May 10, 1976, abandoned.

[51] Int. Cl.$^2$ .................. C07D 333/24; C07D 333/16; C07D 333/00; A01N 9/00

[52] U.S. Cl. .................. 260/332.2 R; 260/329 AM; 260/329 F; 260/332.3 P; 424/275; 424/648

[58] Field of Search ..... 260/329 AM, 329 F, 332.3 P, 260/332.2 R

[56] References Cited

U.S. PATENT DOCUMENTS

3,944,567  3/1976  Asato .............................. 260/332.3 P

*Primary Examiner*—A. Siegel
*Attorney, Agent, or Firm*—H. H. Kline

[57] ABSTRACT

This disclosure describes novel 5,6,7,8-tetrahydro-4H-cyclohepta[b]thiophen-4-amines useful as intermediates for the preparation of animal growth regulants.

21 Claims, No Drawings

SUBSTITUTED TETRAHYDROBENZOTHIOPHENES AND METHOD OF PREPARATION THEREOF

This application is a continuation of my copending U.S. application Ser. No. 684,701, filed May 10, 1976 and now abandoned.

BRIEF SUMMARY OF THE INVENTION

This invention relates to new 5,6,7,8-tetrahydro-4H-cyclohepta[b]thiophen-4-amines and derivatives thereof which may be converted to animal growth regulants. More particularly, this invention relates to novel compounds which may be represented by the following general formulae:

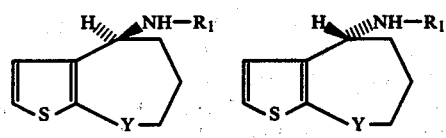

wherein $R_1$ is hydrogen, formyl, alkanoyl having from 2 to 6 carbon atoms, halogen-substituted alkanoyl having from 2 to 6 carbon atoms, or a moiety of the formula:

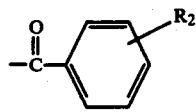

wherein $R_2$ is hydrogen, halogen, nitro, or methoxy; and Y is a divalent radical selected from the group consisting of those of the formulae:

Halogen in the above general formulae is exemplified by fluoro, chloro, bromo, and iodo.

DETAILED DESCRIPTION OF THE INVENTION

The novel compounds of the present invention when $R_1$ is hydrogen are organic bases and thus are capable of forming acid-addition salts with a variety of organic and inorganic salt-forming reagents. Thus, acid-addition salts, formed by admixture of the free base with one equivalent of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic and related acids. The acid-addition salts of these free bases of the present invention are, in general, crystalline solids relatively soluble in water, methanol and ethanol but are relatively insoluble in non-polar organic solvents such as diethyl ether, benzene, toluene, and the like. For purposes of this invention, these free bases are equivalent to their acid-addition salts.

The novel compound of the present invention in accordance with the following formula:

wherein $R_1$ is hydrogen may be readily prepared as the hydrochloride salt by the hydrochloric acid hydrolysis of N-(5,6,7,8-tetrahydro-4H-cyclohepta[b]thien-4-yl)formamide. The free base may be readily obtained by neutralization in aqueous solution followed by extraction with an immiscible organic solvent. The novel compounds of the present invention in accordance with the above formula wherein $R_1$ is other than hydrogen may be prepared in a variety of ways. Formylation may be accomplished by refluxing 5,6,7,8-tetrahydro-4H-cyclohepta[b]thiophen-4-amine with 98% formic acid in an inert solvent such as benzene whilst azeotroping off the water. Alkanoylation or benzoylation may be accomplished by treating 5,6,7,8-tetrahydro-4H-cyclohepta[b]thiophen-4-amine with a compound of the formulae:

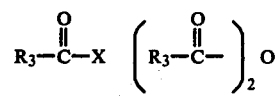

wherein X is chloro or bromo and $R_3$ is alkyl having up to 5 carbon atoms, halogen-substituted alkyl having up to 5 carbon atoms, or a moiety of the formula:

wherein $R_2$ is as hereinabove defined. This reaction may be readily carried out in an inert organic solvent such as benzene, toluene, chloroform, dioxane, etc. in the presence of an acid acceptor such as soda ash, pyridine, trimethylamine, and the like at ambient temperatures to reflux temperatures for a period of time of from 15 to a few hours or more.

The novel compounds of the present invention wherein Y is carbonyl are prepared from the corresponding compounds of the present invention wherein Y is methylene by an oxidation reaction which may be graphically illustrated as follows:

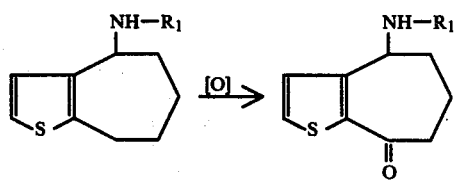

wherein $R_1$ is as defined hereinabove with the proviso that $R_1$ may not be hydrogen. The starting material is reacted with a 2 to 8 mole equivalent, preferably with a 2 to 5 mole equivalent, of an oxidizing agent selected from the group consisting of ceric ammonium nitrate, ceric sulfate, silver oxide, chromic anhydride or sodium bichromate at a temperature between about 0° C. and about 100° C., preferably 20° C. to 60° C., in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid; or chromic anhydride - acetic anhydride, followed by hydrolysis. Other oxidizing agents, such as persulfates, may also be used in the above oxidation reaction if so desired. It is recognized, of course, that many other blocking groups, not included in the above definition of $R_1$, can be used and that while some may give somewhat higher yields or easier workup, the net effect is the same in all cases, that is to protect the —$NH_2$ function during the oxidation step. Included in this category of protecting groups is an imido group, such as phthalimido, wherein the group consists of the $R_1$ and the hydrogen with the associated nitrogen.

The corresponding 8-hydroxy (cis and trans isomers, as defined above) analogs are prepared from the corresponding 8-oxo compounds by reduction with equimolar or excess amounts of sodium borohydride, at a temperature range between about 0° C. and about 75° C., preferably 20° C. to 40° C., in $C_1$-$C_3$ alcohols to afford a mixture of the cis and trans isomers. This reaction may be graphically illustrated as follows:

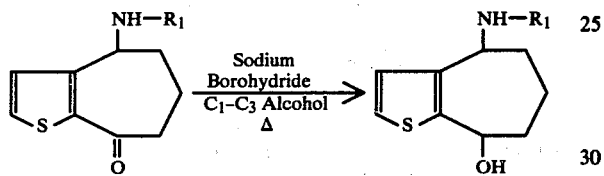

wherein $R_1$ is as defined hereinabove.

The novel compounds of the present invention wherein $R_1$ is other than hydrogen may be readily converted to the corresponding bases wherein $R_1$ is hydrogen by acid or preferably base hydrolysis. For example, hydrolysis in dilute alkali in inert atmosphere at temperatures of from about 50° C. to reflux temperature for a period of time of from 15 minutes to a few hours or more readily provides the corresponding 4-amino compounds.

The novel compounds of the present invention wherein $R_1$ is hydrogen are useful intermediates for the preparation of animal growth regulants as set forth in the following reaction scheme:

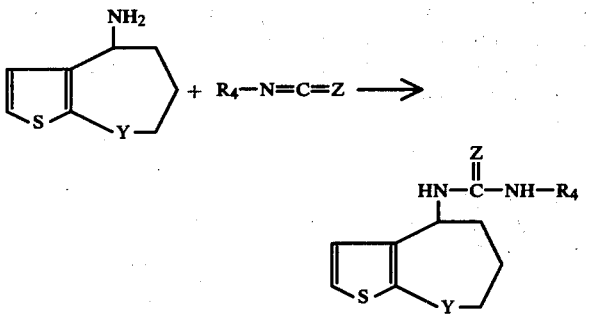

wherein $R_4$ is methyl or ethyl, Z is oxgyen or sulfur, and Y is as hereinabove defined. The reaction can be carried out using approximately equimolar amounts of the isocyanate or isothiocyanate and the amine or amine acid salt. The reaction can be conducted at atmospheric or superatmospheric pressure at a temperature in the range of 0° to 100° C., but is preferably conducted at atmospheric pressure at 0° C. to 70° C. in the presence of an organic solvent. Suitable organic solvents include aprotic aromatic solvents such as benzene, toluene, and xylene; chlorinated hydrocarbon solvents such as methylene chloride, chloroform and dichloroethane; ethers such as tetrahydrofuran, diethyl ether, dimethoxyethane, diethylene glycol dimethyl ether, and dioxane; lower alkyl $C_1$-$C_4$ ketones such as acetone, methyl ethyl ketone, methyl butyl ketone and methyl isobutyl ketone, or mixtures of said solvents.

When the above reaction is carried out using a 5,6,7,8-tetrahydro-4H-cyclohepta[b]thiophen-4-amine acid salt, it is desirable to add an acid acceptor to the reaction mixture. Suitable acid acceptors include trialkylamines such as triethylamine, trimethylamine, pyridine or the like; alkali metal carbonates such as sodium and potassium carbonate; alkaline earth metal carbonates such as calcium carbonate; strong basic ion exchange resins; and aqueous alkali in a 2-phase system using an immiscible hydrocarbon solvent such as benzene or toluene, or a chlorinated hydrocarbon such as chloroform or dichloroethane.

Other useful animal growth regulants may be readily prepared as set forth in the following reaction scheme:

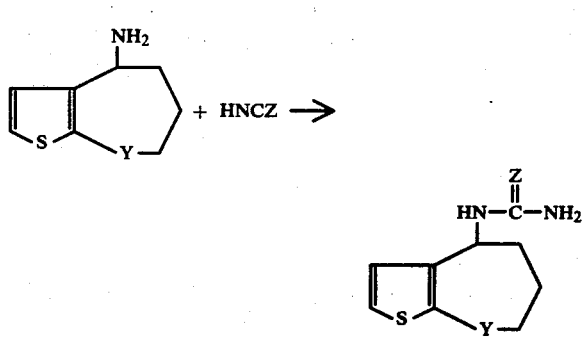

wherein Y is as hereinabove defined and Z is oxygen or sulfur. The reaction can be carried out by reacting the amine or its acid-addition salt with an approximately equimolar amount of sodium or potassium cyanate or thiocyanate. However, it is generally preferable to employ 5% to 50% excess of the cyanate or thiocyanate and to conduct the reaction in a suitable solvent. Suitable solvents include water, polar solvents such as $C_1$-$C_3$ alcohols, tetrahydrofuran, dioxane, ethyleneglycol dimethyl ether, diethylene glycol, dimethyl ether, acetone, methyl ethyl ketone and the like and mixtures thereof; in the pH range of 5 to 7 and preferably at pH 6.

The preparation of the optically active 5,6,7,8-tetrahydro-4H-cyclohepta[b]thiophen-4-amine which is a useful intermediate for the synthesis of the optically active 5,6,7,8-tetrahydro-4H-cyclohepta[b]thien-4-ylureas may be accomplished as follows. The racemic (dl) 5,6,7,8-tetrahydro-4H-cyclohepta[b]thiophen-4-amine is treated with the (+)-N-benzoylglutamic acid to form a water-insoluble salt of (+)-5,6,7,8-tetrahydro-4H-cyclohepta[b]thiophen-4amine in high yield. It is not necessary to employ more than one mole of the resolving acid for each two moles of dl amine as a cheaper acid, preferably acetic acid, can be substituted for the balance of required acid. In this way it is possible to obtain a high yield of the desired (+)-amine based on the resolving acid. The resolved salt, (+)-5,6,7,8-tetrahydro-4H-cyclohepta[b]thiophen-4-amine. (+)-N-benzoylglutamic acid, is treated with alkali which liberates the (+)-amine which separates as an insoluble phase. It can be mechanically separated from the aqueous phase or extracted conventionally with a suitable solvent.

The (−)-amine which remains in solution is then recovered and treated with (−)-N-benzoylglutamic acid and acetic acid in the above-mentioned manner with the molarity adjusted to the amount of (+) amine obtained from the initial resolution. The salt, (−)-5,6,7,8-tetrahydro-4H-cyclohepta[b]thiophen-4-amine. (−)-N-benzoylglutamic acid, crystallizes and is then treated in the above-mentioned manner to give the (−)-amine.

With respect to optical isomers, the most preferred optically active ureido compounds for enhancement of growth in animals are those which are derived from the (+)-5,6,7,8-tetrahydro-4H-cyclohepta[b]thiophen-4-amine. Thus, the following reaction schemes will exemplify the sequence in the preparation of the optically active compounds.

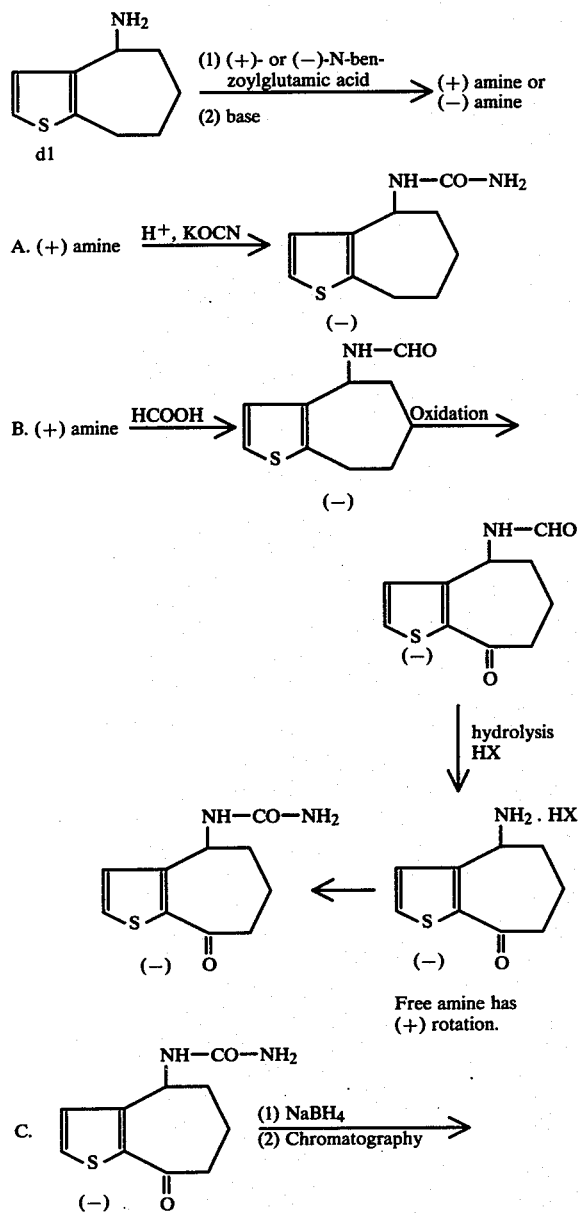

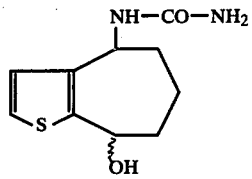

Isomer A (−)
Isomer B (−)

The separation of cis and trans-(−)-5,6,7,8-tetrahydro-7-hydroxy-4H-cyclohepta[b]thien-4-ylureas is readily achieved by using preparative high-pressure liquid chromatography on silica gel with 1800 ml. of hexane/1000 ml. of CHCl$_3$/425 ml. of MeOH at a flowrate of 40 ml./minute. Since the configurations have not been established, the isomers are designated as Isomer A and Isomer B. Conversely, if (−)-5,6,7,8-tetrahydro-4H-cyclohepta[b]thiophen-4-amine is used in the above sequence, the resulting derivatives of the opposite sign are obtained.

Because 5,6,7,8-tetrahydro-7-oxo-4H-cyclohepta[b]thiophen-4-amine is also a useful intermediate, this compound in its optically active form is desirable. Thus, dl-5,6,7,8-tetrahydro-7-oxo-4H-cyclohepta[b]thiophen-4-amine is readily resolved with (+)-tartaric acid in methanol as follows:

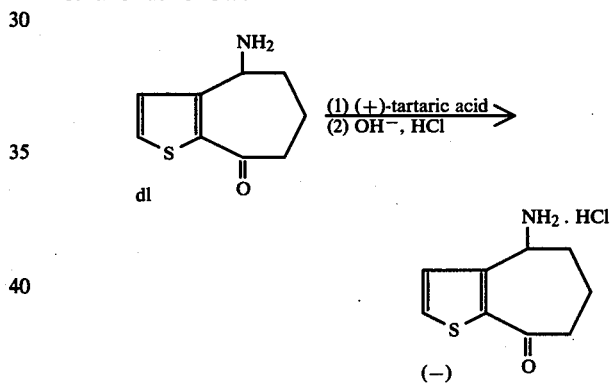

and the resulting crystalline tartrate salt is recrystallized from 95% ethanol. The salt is decomposed with aqueous NaOH solution and the optically active keto-amine is separated by conventional extraction and acidified with HCl to afford (−)-5,6,7,8-tetrahydro-7-oxo-4H-cyclohepta[b]thiophen-4-amine hydrochloride, which can be used in the manner described above.

The present invention is further illustrated by the preparation of representative examples as set forth below, as well as testing data on typical animal growth regulants.

EXAMPLE 1

Preparation of 1-methyl-3-(5,6,7,8-tetrahydro-4H-cyclohepta[b]thien-4-yl)urea 5,6,7,8-Tetrahydro-4H-cyclohepta[b]thiophen-4-one is converted to N-(5,6,7,8-tetrahydro-4H-cyclohepta[b]thien-4-yl)formamide, m.p. 164°–166° C., by the method of Kloetzel et al., Journal of Organic Chemistry 18, 1511 (1953). Hydrolysis of the formamide is accomplished by refluxing for one hour in 1N hydrochloric acid and evaporating to dryness to afford 5,6,7,8-tetrahydro-4H-cyclohepta[b]thiophen-4-amine hydrochloride, m.p. 233°–236° C. dec. The amine hydrochloride is then allowed to react with methyl isocyanate in dry tetrahydrofuran as solvent in the presence of a stoichiometric equivalent of triethylamine to afford 1-methyl-3-(5,6,7,8-tetrahydro-4H-cyclohepta[b]thien-4-yl)urea, m.p. 220°–222° C.

Similarly, by substituting ethyl isothiocyanate for methyl isocyanate in the above procedure there is obtained 1-ethyl-3-(5,6,7,8-tetrahydro-4H-cyclohepta[b]thien-4-yl)-2-thiourea, m.p. 117°–120° C.

EXAMPLE 2

Preparation of 5,6,7,8-tetrahydro-4H-cyclohepta[b]thien-4-ylurea

A mixture of 50 grams of 5,6,7,8-tetrahydro-4H-cyclohepta[b]thiophen-4-amine hydrochloride in 100 ml. of water is stirred at about 15° C. and a solution of 23.1 grams of potassium cyanate in 100 ml. of water is added dropwise. After completion of the addition, the mixture is warmed slowly to 70°–75° C. and held there for one hour. The mixture is cooled and the white solid is collected by filtration and washed with water. The solid is air-dried, pulverized, and washed with acetonitrile. Upon drying, this crude product is treated with hot acetone whereby there is obtained 5,6,7,8-tetrahydro-4H-cyclohepta[b]thien-4-ylurea, m.p. 217° C. dec.

EXAMPLE 3

Preparation of 1-(methoxymethyl)-3-(5,6,7,8-tetrahydro-4H-cyclohepta[b]thien-4-yl)urea In 150 ml. of methanol is stirred 8.24 grams of 5,6,7,8-tetrahydro-4H-cyclohepta[b]thien-4-ylurea and 2.1 grams of sodium hydroxide pellets followed by 2.31 grams of paraformaldehyde in 50 ml. of methanol. The mixture is heated at reflux for 10 hours and cooled to afford crystals which are collected. The filtrate is evaporated to dryness and the residue is washed with water to afford more solid. Recrystallization of the combined fractions from acetone-hexane gives 1-(methoxymethyl)-3-(5,6,7,8-tetrahydro-4H-cyclohepta[b]thien-4-yl)urea, m.p. 197°–201° C. dec.

EXAMPLE 4

Preparation of 5,6,7,8-tetrahydro-4H-8-oxocyclohepta[b]thien-4-ylurea

In 375 ml. of 50% aqueous acetic acid is dissolved 6 grams of 5,6,7,8-tetrahydro-4H-cyclohepta[b]thien-4-ylurea, and 75 grams of ceric ammonium nitrate is added portionwise over a 10 minute period with stirring at 25°–35° C. The pale orange solution is stirred for another five minutes and 100 ml. of water is added. The solution is extracted twice with ethyl acetate (450 ml. and 350 ml.) and the combined extracts are washed with 100 ml. of water. The organic extract is evaporated to dryness in vacuo and the brown residue is recrystallized from methanol to afford 5,6,7,8-tetrahydro-4H-8-oxocyclohepta[b]thien-4-ylurea, m.p. 246°–248° C. dec.

EXAMPLE 5

Mouse Growth Regulant Tests

CFI female mice from Carworth Farms are received when they are six weeks old. They are housed ten to a cage in air-conditioned rooms (72° F. to 76° F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of ten and assigned at random to the different treatments. The concentration of the different compounds in the diet is indicated in the following tables. Twelve days later the mice are weighed again and the experiment terminated. At least three cages (30 mice) of untreated controls are included in each test. Test data are provided in Table I below wherein data are reported as percent weight gain over controls. Unless otherwise indicated in this table, all compounds tested were dl-racemic mixtures. The following is a description of the diet to which the growth promoting compounds were added.

| DIET GUARANTEED ANALYSIS | |
|---|---|
| Crude protein not less than | 23.0% |
| Crude fat not less than | 4.5% |
| Crude fiber not more than | 6.0% |
| Ash not more than | 9.0% |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin B$_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide.

TABLE I

Effectiveness of 5,6,7,8-Tetrahydro-4H-cyclohepta[b]thien-4-ylureas as Animal Growth Promoting Agents
Reported as Percent Weight Gain Over Controls
Using Mice as the Test Animal

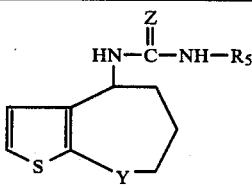

| Rate ppm in Diet | Y | Z | R$_5$ | % Weight Gain Over Controls |
|---|---|---|---|---|
| 400 | \CH$_2$— | O | H | 54 |
| 400 | \CH$_2$— | O | —CH$_3$ | 41 |
| 400 | \CH$_2$— | S | —C$_2$H$_5$ | 40 |
| 400 | \CH$_2$— | O | —CH$_2$OCH$_3$ | 10 |
| 400 | \C=O | O | H | 68.8 |

TABLE I-continued
Effectiveness of 5,6,7,8-Tetrahydro-4H-cyclohepta[b]thien-4-ylureas as Animal Growth Promoting Agents Reported as Percent Weight Gain Over Controls Using Mice as the Test Animal $$\underset{\substack{\text{HN—C—NH—R}_5\\\text{}}}{\overset{\overset{Z}{\parallel}}{\underset{\substack{\diagup\\S}}{\bigcirc}}\,\underset{\substack{\diagdown\\Y}}{\bigcirc}}$$

| Rate ppm in Diet | Y | Z | $R_5$ | % Weight Gain Over Controls |
|---|---|---|---|---|
| 200 | \CH—<br>/<br>OH | O | H | 157.8 |

EXAMPLE 6

Preparation of cis and trans-5,6,7,8-tetrahydro-8-hydroxy-4H-cyclohepta[b]-thien-4-ylurea A sample of 1.72 g. of 5,6,7,8-tetrahydro-8-oxo-4H-cyclohepta[b]thien-4-ylurea is stirred in 120 ml. of absolute ethanol and 0.5 g. of sodium borohydride is added. After 5.5 hours, 50 ml. of water is added to the mixture and the mixture is evaporated to dryness in vacuo. Acetone is added to the residue and the mixture is evaporated to dryness. The residue is then extracted with 3×75 ml. portions of boiling acetone, the acetone solution being decanted each time. The combined acetone solutions are filtered and evaporated to dryness. The residue is then washed with diethyl ether and the insoluble solid (contains some gum) is crystallized from methanol/ethyl acetate to afford 0.148 g. of yellow solid. The mother liquor is evaporated to dryness and chromatographed on preparative thin-layer silica-gel chromatographic plates with 15 parts methanol/85 parts chloroform. A fraction melting at 171°–175° C. is then obtained after separation and recrystallization from methanol/ethyl acetate. This material analyzes acceptably (carbon, hydrogen and nitrogen) for the title compound and the infrared spectrum also supports the structure. A second fraction melting at 169°–172° C. is also obtained and its infrared spectrum is virtually identical with that of the above-mentioned fraction.

EXAMPLE 7

Preparation of N-(5,6,7,8-tetrahydro-4H-cyclohepta[b]thien-4-yl)acetamide

A 1.45 gram sample of 5,6,7,8-tetrahydro-4H-cyclohepta[b]thiophen-4-amine hydrochloride is stirred in 20 ml. of water and 10 ml. of 10% aqueous sodium hydroxide solution is added. The free amine, 5,6,7,8-tetrahydro-4H-cyclohepta[b]thiophen-4-amine, is extracted with methylene chloride and the extract (100 ml.) is washed with water, dried under nitrogen atmosphere, and evaporated to dryness. The amine is then dissolved in 7 ml. of toluene and the solution is added to a solution of 2 ml. of acetic anhydride in 5 ml. of toluene under nitrogen atmosphere. After the addition is completed, the reaction mixture is stirred at room temperature for an hour and then heated to 90° C. for an hour. The mixture is cooled to room temperature, diluted with diethyl ether, and the fluffy white title compound is collected and dried. The filtrate is evaporated to dryness and the residue is stirred with diethyl ether/hexane. The insoluble solid is collected and dried to afford additional title compound. The first fraction (1.25 g.) melts at 179°–180° C. and the second fraction (0.140 g.) melts at 177.5°–179° C.

EXAMPLE 8

Preparation of N-(5,6,7,8-tetrahydro-4H-8-oxocyclohepta[b]thien-4-yl)acetamide

A 1.32 gram sample of N-(5,6,7,8-tetrahydro-4H-cyclohepta[b]thien-4-yl)acetamide is added to 13 ml. of water and 6.5 ml. of glacial acetic acid. The mixture is cooled to 15° C. and 14.3 grams of ceric ammonium nitrate is added over 15 minutes. An additional 2.5 ml. of glacial acetic acid and 5 ml. of water are added and the mixture is stirred at room temperature. After half an hour, another 1 gram of ceric ammonium nitrate is added along with 5 ml. of glacial acetic acid. The mixture is stirred for an hour, a solution of 3.96 grams of $Na_2SO_4$ in 25 ml. of water is added followed by 10 ml. of glacial acetic acid. The mixture is filtered, the filter cake is washed well with water and the combined filtrates are extracted with methylene chloride (3×50 ml.). The extracts are washed with brine, dried over $Na_2SO_4$ and evaporated to dryness. The residue is stirred in diethyl ether and scratched to afford the title compound, which is collected by filtration and dried. The yellowish product melts at 103°–120° C. with decomposition.

Similarly, the following amides represented by structure B are prepared by substituting amides represented by structure A for N-(5,6,7,8-tetrahydro-4H-cyclohepta[b]thien-4-yl)acetamide in the above sequence:

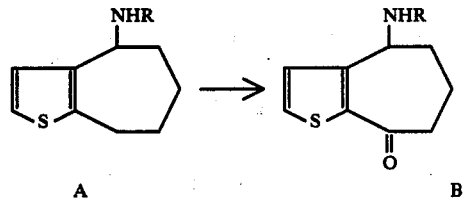

wherein R is: CHO, $C_2H_5CO$, n—$C_3H_7$—CO, i—$C_3H_7$—CO, n—$C_4H_9$—CO, 2—$C_4H_9$—CO, t—$C_4H_9$—CO, i—$C_4H_9$—CO, n—$C_5H_{11}$—CO, $(CH_3)_3C$—$CH_2$—CO, $ClCH_2$—CO, $Cl_3C$—CO, $CF_3$—CO, $ClCH_2$—$CH_2$—CO, benzoyl, 2-chlorobenzoyl, 3-chlorobenzoyl, 4-chlorobenzoyl, 2-nitrobenzoyl, 4-nitrobenzoyl, 3-nitrobenzoyl, 2-methoxybenzoyl, 3-methoxybenzoyl, or 4-methoxybenzoyl.

Compounds A are readily prepared by allowing 5,6,7,8-tetrahydro-4H-cyclohepta[b]thiophen-4-amine to react with an equivalent amount of $$\underset{\text{R—C—Cl/pyridine/benzene or }(R—C)_2O/\text{benzene,}}{\overset{O}{\parallel}\qquad\qquad\overset{O}{\parallel}}$$

wherein R is as defined above. The reaction mixture is allowed to stir at room temperature or heated until the reaction is complete. The product A is then collected by filtration or obtained by evaporating the reaction mixture to dryness in vacuo and washing the product with water and dilute hydrochloric acid.

EXAMPLE 9

Preparation of 5,6,7,8-tetrahydro-4H-8-oxocyclohepta[b]thiophen-4-amine

A 0.1 gram sample of N-(5,6,7,8-tetrahydro-4H-8-oxocyclohepta[b]thien-4-yl)acetamide is stirred in 5 ml. of water and 5 ml. of concentrated aqueous hydrochloric acid. The mixture is heated to reflux for 3.5 hours and cooled. The solution is filtered and the filtrate is extracted with 30 ml. of methylene chloride, which is washed with 30 ml. of water. The combined water wash and acidic filtrate are evaporated to dryness and the residue is stirred in acetone/diethyl ether to afford a gummy solid, m.p. 130°–160° C. This crude product contains mainly the amine hydrochloride, which is then neutralized with 10% aqueous NaOH solution to afford the title compound. The oily title compound is extracted with $CHCl_3$ and after drying over $Na_2SO_4$. The solution is evaporated to dryness to give 5,6,7,8-tetrahydro-4H-8-oxocyclohepta[b]thiophen-4-amine.

Similarly, the following amides represented by structure C, wherein $R_1$ is as defined below, in place of N-(5,6,7,8-tetrahydro-4H-8-oxocyclohepta[b]thien-4-yl)acetamide also affords 5,6,7,8-tetrahydro-4H-8-oxocyclohepta[b]thiophen-4-amine.

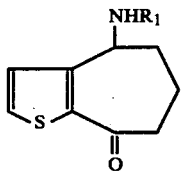

C

Wherein $R_1$ is CHO, $ClCH_2$—CO, n—$C_5H_{11}$—CO, $C_6H_5$—CO, $CF_3$—CO, $(CH_3)_3C$—CO and $CCl_3$—CO.

EXAMPLE 10

Preparation of cis and trans-5,6,7,8-tetrahydro-8-hydroxy-4H-cyclohepta[b]thiophen-4-amine A sample of a cis/trans mixture of N-(5,6,7,8-tetrahydro-8-hydroxy-4H-cyclohepta[b]thien-4-yl)acetamide is added to 2 equivalents of KOH in water/ethylene glycol mixture. The mixture is heated at reflux under nitrogen atmosphere until starting material is no longer detectable by thin-layer chromatography. The mixture is cooled, diluted with water and extracted exhaustively with $CHCl_3$. The chloroform extract is added to an equal volume of water and acidified with hydrochloric acid until the mixture is at pH 2. The mixture is then extracted with $CHCl_3$ and then the remaining aqueous solution is made alkaline with NaOH solution. The alkaline solution is then extracted with $CHCl_3$ exhaustively and the extracts are dried over $MgSO_4$ and evaporated to dryness to afford the title compound.

Similarly, substitution of amides represented by structure D, wherein $R_1$ is as defined below, in place of N-(5,6,7,8-tetrahydro-8-hydroxy-4H-cyclohepta[b]thien-4-yl)acetamide also affords the title amine:

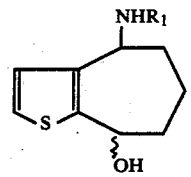

D wherein $R_1$ is CHO, $Cl_3$—CO, $ClCH_2$—CO, n—$C_3H_7$—CO, n—$C_5H_{11}$—CO, $C_6H_5$—CO, or $CF_3$—CO.

EXAMPLE 11

Preparation of cis and trans-N-(5,6,7,8-tetrahydro-8-hydroxy-4H-cyclohepta[b]thien-4-yl)acetamide In the manner described in Example 6, N-(5,6,7,8-tetrahydro-4H-8-oxocyclohepta[b]thien-4-yl)acetamide is reduced with $NaBH_4$ to afford a mixture of cis and trans-N-(5,6,7,8-tetrahydro-8-hydroxy-4H-cyclohepta[b]thien-4-yl)acetamide.

Similarly, the following compounds represented by structure F are prepared by substituting compounds represented by structure E for N-(5,6,7,8-tetrahydro-4H-8-oxocyclohepta[b]thien-4-yl)acetamide:

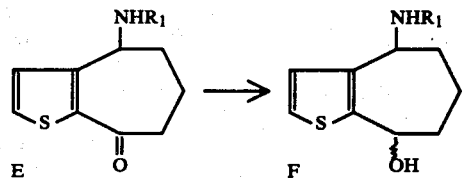

wherein $R_1$ is CHO, $ClCH_2$—CO, $Cl_3C$—CO, n—$C_2H_5$—CO, $CF_3$—CO, n—$C_5H_6$—CO, benzoyl, 4-chlorobenzoyl, 2-chlorobenzoyl, 3-chlorobenzoyl, 4-nitrobenzoyl, 3-nitrobenzoyl, 2-nitrobenzoyl, 4-methoxybenzoyl, 3-methoxybenzoyl, or 2-methoxybenzoyl.

EXAMPLE 12

Preparation of 1-methyl-3-(5,6,7,8-tetrahydro-4H-8-oxocyclohepta[b]thien-4-yl)urea In methylene chloride, 5,6,7,8-tetrahydro-4H-8-oxocyclohepta[b]thiophen-4-amine is stirred under nitrogen atmosphere and an equivalent amount of methyl isocyanate in methylene chloride is added slowly. The mixture is stirred at room temperature for an hour and then heated at reflux for 0.5 hour. The mixture is then evaporated to dryness in vacuo and the solid residue is triturated with diethyl ether. The title compound is collected by filtration.

EXAMPLE 13

Preparation of 1-methyl-3-(5,6,7,8-tetrahydro-8-hydroxy-4H-cyclohepta[b]thien-4-yl)urea A solution of 5,6,7,8-tetrahydro-8-hydroxy-4H-cyclohepta[b]thiophen-4-amine is stirred under nitrogen atmosphere and an equivalent amount of methyl isocyanate in methylene chloride is added slowly. After the addition is completed, the mixture is stirred at room temperature for one hour and heated to reflux for 0.5 hour. The mixture is then evaporated to dryness in vacuo and the residue is triturated with diethyl ether. The title compound is collected by filtration and dried.

I claim:
1. A compound selected from the group consisting of those of the formulae:

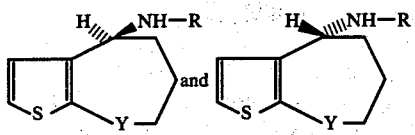

wherein R is hydrogen, formyl, alkanoyl having from 2 to 6 carbon atoms, halogen-substituted alkanoyl having from 2 to 6 carbon atoms, or a moiety of the formula:

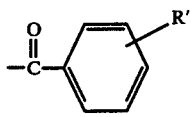

wherein R' is hydrogen, halogen, nitro, or methoxy; Y is a divalent radical selected from the group consisting of those of the formulae:

and the acid-addition salts thereof when R is hydrogen.

2. A compound selected from the group consisting of the dextrorotatory enantiomorph, the levorotatory enantiomorph, and the racemic mixture thereof of a compound of the formula:

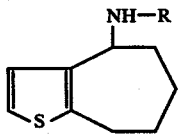

wherein R is hydrogen, formyl, alkanoyl having from 2 to 6 carbon atoms, halogen-substituted alkanoyl having from 2 to 6 carbon atoms, or a moiety of the formula:

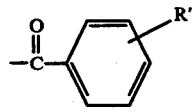

wherein R' is hydrogen, halogen, nitro, or methoxy; and the acid-addition salts thereof when R is hydrogen.

3. The dextrorotatory enantiomorph according to claim 2 wherein R is hydrogen; d-5,6,7,8-tetrahydro-4H-cyclohepta[b]thiophen-4-amine.

4. The levorotatory enantiomorph according to claim 2 wherein R is hydrogen; l-5,6,7,8-tetrahydro-4H-cyclohepta[b]thiophen-4-amine.

5. The racemic mixture according to claim 2 wherein R is hydrogen; dl-5,6,7,8-tetrahydro-4H-cyclohepta[b]thiophen-4-amine.

6. The racemic mixture according to claim 2 wherein R is formyl; dl-N-(5,6,7,8-tetrahydro-4H-cyclohepta[b]thien-4-yl)formamide.

7. The racemic mixture according to claim 2 wherein R is acetyl; dl-N-(5,6,7,8-tetrahydro-4H-cyclohepta[b]thien-4-yl)acetamide.

8. A compound selected from the group consisting of the dextrorotatory enantiomorph, the levorotatory enantiomorph, and the racemic mixture thereof of a compound of the formula:

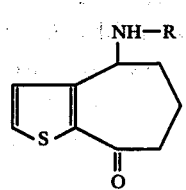

wherein R is hydrogen, formyl, alkanoyl having from 2 to 6 carbon atoms, halogen-substituted alkanoyl having from 2 to 6 carbon atoms, or a moiety of the formula:

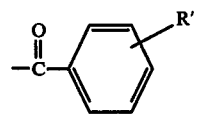

wherein R' is hydrogen, halogen, nitro, or methoxy; and the acid-addition salts thereof when R is hydrogen.

9. The dextrorotatory enantiomorph according to claim 8 wherein R is hydrogen; d-5,6,7,8-tetrahydro-4H-8-oxocyclohepta[b]thiophen-4-amine.

10. The levorotatory enantiomorph according to claim 8 wherein R is hydrogen; l-5,6,7,8-tetrahydro-4H-8-oxocyclohepta[b]thiophen-4-amine.

11. The racemic mixture according to claim 8 wherein R is hydrogen; dl-5,6,7,8-tetrahydro-4H-8-oxocyclohepta[b]thiophen-4-amine.

12. The racemic mixture according to claim 8 wherein R is acetyl; dl-N-(5,6,7,8-tetrahydro-4H-8-oxocyclohepta[b]thien-4-yl)acetamide.

13. A compound selected from the group consisting of the cis-dextrorotatory enantiomorph, the cis-levorotatory enantimorph, the racemic mixture of the cis-enantiomorphs, the trans-dextrorotatory enantiomorph, the trans-levorotatory enantiomorph, and the racemic mixture of the trans-enantiomorphs of a compound of the formula:

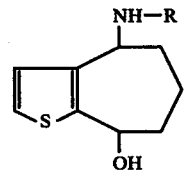

wherein R is hydrogen, formyl, alkanoyl having from 2 to 6 carbon atoms, halogen-substituted alkanoyl having from 2 to 6 carbon atoms, or a moiety of the formula:

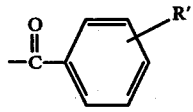

wherein R' is hydrogen, halogen, nitro, or methoxy; and the acid-addition salts thereof when R is hydrogen.

14. The cis-dextrorotatory enantiomorph according to claim 13 wherein R is hydrogen; d-cis-5,6,7,8-tetrahydro-8-hydroxy-4H-cyclohepta[b]thiophen-4-amine.

15. The cis-levorotatory enantiomorph according to claim 13 wherein R is hydrogen; l-cis-5,6,7,8-tetrahydro-8-hydroxy-4H-cyclohepta[b]thiophen-4-amine.

16. The cis-racemic mixture according to claim 13 wherein R is hydrogen; dl-cis-5,6,7,8-tetrahydro-8-hydroxy-4H-cyclohepta[b]thiophen-4-amine.

17. The trans-dextrorotatory enantiomorph according to claim 13 wherein R is hydrogen; d-trans-5,6,7,8-tetrahydro-8-hydroxy-4H-cyclohepta[b]thiophen-4-amine.

18. The trans-levorotatory enantiomorph according to claim 13 wherein R is hydrogen; l-trans-5,6,7,8-tetrahydro-8-hydroxy-4H-cyclohepta[b]thiophen-4-amine.

19. The trans-racemic mixture according to claim 13 wherein R is hydrogen; dl-trans-5,6,7,8-tetrahydro-8-hydroxy-4H-cyclohepta[b]thiophen-4-amine.

20. The cis-racemic mixture according to claim 13 wherein R is acetyl; dl-cis-N-(5,6,7,8-tetrahydro-8-hydroxy-4H-cyclohepta[b]thien-4-yl)acetamide.

21. The trans-racemic mixture according to claim 13 wherein R is acetyl; dl-trans-N-(5,6,7,8-tetrahydro-8-hydroxy-4H-cyclohepta[b]thien-4-yl)acetamide.

* * * * *